United States Patent [19]

Sato et al.

[11] Patent Number: 5,200,429
[45] Date of Patent: Apr. 6, 1993

[54] ACNE VULGARIS TREATING

[75] Inventors: Toshiya Sato, Tokyo; Satoko Tsukada, Kanagawa; Hamako Hata; Kenya Ishida, both of Tokyo, all of Japan

[73] Assignee: Takasago International Corporation, Tokyo, Japan

[21] Appl. No.: 765,739

[22] Filed: Sep. 26, 1991

[30] Foreign Application Priority Data

Sep. 28, 1990 [JP] Japan ................................ 2-257226

[51] Int. Cl.$^5$ ............................................ A61K 31/015
[52] U.S. Cl. ................................. 514/766; 514/859
[58] Field of Search .......................... 514/766, 859

[56] References Cited

FOREIGN PATENT DOCUMENTS 0308210 9/1988 European Pat. Off. .
63-150208 6/1988 Japan .

OTHER PUBLICATIONS

Chemical Abstracts 110:237000c (1989).
Chemical Abstracts 113:165123g (1990).
M. Yatagai et al., *Biochemical Systematics and Ecology*, 13(4), 377–385 (1985).
Osamu Okuda, *Comprehensive Bibliography of Perfume Chemistry*, vol. I, published by Hirokawa Publishing Co. on Jul. 5, 1967.
J. A. Morris et al., *Journal of the American Oil Chemists' Society*, 56, 595–603 (1979).
N. Diaz et al., *An Real Acad. Farm.*, 54:526–531 (1988).
B. B. Dey et al., Indian Perfumer, 28(2), pp. 82–87, 1984.
Masaaki Ito et al., J. Antibact. Antifung. Agents, 8(1), pp. 3–6, 1980.

*Primary Examiner*—Leonard Schenkman
*Attorney, Agent, or Firm*—Sughrue, Mion, Zinn, Macpeak & Seas

[57] ABSTRACT

An acne vulgaris treating and preventing topica, which comprises, as an active ingredient, at least one compound selected from the group consisting of caryophyllene, cedrene, longifolene and thujopsene. The topica exhibits sufficient inhibitory activity on proliferation of *Propionibacterium acnes*, a pathogenic bacterium causing acne vulgaris, at a small therapeutic dose without causing skin irritation.

3 Claims, No Drawings

ACNE VULGARIS TREATING

FIELD OF THE INVENTION

This invention relates to an acne vulgaris treating and preventing topica, and more particularly to a topica which is markedly effective to treat or prevent acne vulgaris, containing, as an active ingredient, at least one compound selected from caryophyllene, cedrene, longifolene and thujopsene, which compounds have bactericidal or inhibitory activity on *Propionibacterium acnes*, a pathogenic bacterium causing acne vulgaris.

BACKGROUND OF THE INVENTION

Acne vulgaris is a skin disease of youths involving comedos, papulae, pustules, etc. appearing on the face, the center of the chest, the upper part of the back, etc. Main causes of acne vulgaris include (1) excessive secretion of sebum, (2) stricture of hair-follicles, and (3) proliferation of *Propionibacterium acnes*, one of Gram positive anaerobic bacteria, in the pilosebaceous gland.

Conventional treatments of acne vulgaris are focused on removal of the above-described three main causes. For example, female hormones are applied to suppression of sebum secretion; keratolytic substances, e.g., salicylic acid, resorcin, etc. are applied to elimination of stricture of hair-follicles; and bactericidal disinfectants, e.g., Chlorhexidine Gluconate, is applied to inhibition of proliferation of the bacterium.

Caryophyllene, cedrene, longifolene, and thujopsene which are used as active ingredients in the present invention are known substances belonging to sesquiterpene hydrocarbons which can easily be isolated from trees by extraction and have hitherto been utilized as raw materials of compounded perfumes, such as soap perfumes, or raw materials in perfume production. It is known that these substances generally have weak antibacterial activity as one of physiological activities, and there is found no literature referring to utility as antibacterials. For instance, B. B. Dey, et al. report in *Indian Perfumer*, 28(2), 82-87 (1984) that antimicrobial tests on several fungi, *Escherichia coli*, etc. revealed strong antimicrobial activity of eugenol known to be present in clove oil similarly to caryophyllene but no activity of caryophyllene. Further, Itoh Masaaki, et al. report in *J. Antibact. Antifung. Agents*, 8(1), 3-6 (1980) that any substantial antimicrobial activity on various molds, *Bacillus subtilis*, *Escherichia coli*, and *Pseudomonas aeruginosa* was not exhibited by thujopsene per se extracted from hiba oil but by some of derivatives synthesized therefrom.

With reference to treatment of acne vulgaris by a plant component as an active ingredient, JP-A-63-150208 (the term "JP-A" as used herein means an "unexamined published Japanese patent application" discloses that an extract of trees of the hinoki family, e.g., *Thujopsis dolabrata* Sieb, et Zucc., exhibits antimicrobial activity on *Propionibacterium acnes* and can be incorporated into agents for topical application to the skin. However, the publication does not refer to isolation of the active ingredient. Further, JP-A-1-151522 corresponding to Canadian Patent 1,273,576 and EP-A-0 308 210 proposes to treat acne vulgaris with eucalyptol, menthol or thymol included in monoterpene alcohols in combination with other active ingredients. However, there is no literature on cases of using a sesquiterpene hydrocarbon for treatment of acne vulgaris or on inhibitory or bactericidal activity of a sesquiterpene hydrocarbon on *Propionibacterium acnes*.

Bactericidals conventionally used for inhibition of proliferation of bacteria as an approach to treatment of acne vulgaris, such as Chlorhexidine Gluconate, have side effects of causing erythema or exfoliation, causing extreme skin roughening and skin irritation. It has therefore been difficult to obtain the full effect of such bactericidals due to their limited allowable dose.

SUMMARY OF THE INVENTION

An object of the present invention is to provide an acne vulgaris treating and preventing topica containing, as an active ingredient, a plant component which are highly effective for treating acne vulgaris and causes no serious side effect. The inventors have extensively investigated on an acne vulgaris treating and preventing topica having sufficient inhibitory activity on proliferation of *Propionibacterium acnes*, a pathogenic bacterium causing acne vulgaris, at a small therapeutic dose without causing skin irritation.

As a result, it was found that caryophyllene, cedrene, longifolene, and thujopsene which are safe to the skin and have conventionally been used as perfumes have powerful antimicrobial activity against *Propionibacterium acnes* and thus accomplished the above object of the present invention.

The present invention relates to an acne vulgaris treating and preventing topica comprising, as an active ingredient, at least one compound selected from the group consisting of caryophyllene, cedrene, longifolene and thujopsene, in an amount effective to inhibit proliferation of *Propionibacterium acnes* and carriers or diluents acceptable for topical application.

DETAILED DESCRIPTION OF THE INVENTION

The topica of the present invention may have any arbitrary dose form, such as cosmetic lotions, emulsions, creams, packs, aqueous ointments, and oily ointments and may be applied to various usage such as drugs, quasi-drugs, cosmetics and sanitary compositions.

Caryophyllene, cedrene, longifolene, and thujopsene which are used as an active ingredient can easily be obtained from essential oils used as perfumes or raw materials of perfumes by distillation or the like means. Caryophyllene can be obtained from clove oil (an essential oil obtained by steam distillation of dried buds (crude drug) of *Eugenia caryophyllata* before blooming) or clove leaf oil (an essential oil obtained by distillation of the leaves and twigs of *Eugenia caryophyllata*) as a fraction having a boiling point of 118° to 121° C./10 mmHg. Cedrene can be obtained from ceder wood oil (an essential oil obtained by steam distillation of the trunk of *Juniperus mexicana* or *Juniperus virciniana*) as a fraction having a boiling point of 121° to 125° C./12 mmHg. Longifolene can be obtained from indian turpentine oil (an essential oil obtained from the trunk of *Pinus longifolia*, etc.) as a fraction having a boiling point of 150° to 151° C./36 mmHg. Thujopsene can be obtained from an essential oil obtained from the trunk of *Thujopsis dolabrata* as a fraction having a boiling point of 118 to 120° C./10 mmHg.

The acne vulgaris treating topica of the present invention may contain the above-described active ingredients alone or in combination two or more. These active ingredients manifest their effects in a total content of 0.001% by weight, and sufficient efficacy can be obtained in a total content of 1% by weight. Accordingly, the active ingredients are used at a total content of from about 0.001 to 1% by weight, and preferably from 0.01 to 1% by weight, based on the weight of the topical composition.

Other components which can be used in the acne vulgaris treating and preventing topica of the invention are appropriately selected according to the dose form from those commonly employed for topica, such as surface active agents, moisture retaining agents, lower alcohols, water, thickeners, oily bases, ultraviolet absorbents, perfumes, antioxidants, chelating agents, colorants, antiseptics, antifungal agents, and so on. Further, to broaden the range of application as medicine or to heighten certainty of the effects, the agent may further contain other active ingredients, such as female hormones and salicylic acid.

The acne vulgaris treating and preventing topica of the present invention is preferably applied to the affected part 1 to 3 times a day in proper doses.

The present invention is now illustrated in greater detail by way of Preparation Example and Antimicrobial Test Example for the active ingredients, Formulation Examples, and Antimicrobial Test Example and Clinical Test Example for the preparation, but it should be understood that the present invention is not deemed to be limited thereto. All the percents, parts, and ratios are by weight unless otherwise indicated.

PREPARATION EXAMPLE

Clove leaf oil was distilled under reduced pressure to obtain caryophyllene as a fraction having a boiling point of 118° to 121° C./10 mmHg in a yield of about 30%.

The trunk of *Juniperus virginiana* was steam distilled to obtain ceder wood oil, which was further distilled under reduced pressure to obtain an $\alpha$- and $\beta$-cedrene mixture ($\alpha:\beta$=ca. 8:2) as a fraction having a boiling point of 121 to 125° C./12 mmHg in a yield of about 60%.

Indian turpentine oil was distilled under reduced pressure to obtain longifolene as a fraction having a boiling point of 150° to 151° C./36 mmHg in a yield of about 30%.

An essential oil of the trunk of *Thujopsis dolabrata* was distilled under reduced pressure to obtain thujopsene as a fraction having a boiling point of 118° to 120° C./10 mmHg in a yield of about 50%.

The structure of each of the compounds obtained above was confirmed by comparing the gas chromatogram and mass spectrum with those of a standard sample.

TEST EXAMPLE 1

Antimicrobial Activity of Active Ingredient

The minimum inhibitory concentration (MIC) of caryophyllene, cedrene, longifolene, and thujopsene obtained in Preparation Example against *Propionibacterium acnes* (ATCC 11827) was determined as follows.

The test compound was added to a 4.6% ABCM bouillon aqueous solution (prepared by dissolving 46 g of an ABCM bouillon medium produced by Eiken Kagaku K. K. in 1 l of distilled water) in a concentration of 100 μg/ml, and the solution was stepwise diluted two times with the same medium, followed by sterilization.

A 5 ml aliquot of the solution was put in a test tube and inoculated with 0.1 ml of the culture of *Propionibacterium acnes* which had been preliminarily cultured so as to have a cell density of $5 \times 10^8$ cells/ml. The system was static-cultured under anaerobic conditions at 37° C. for 48 hours, and the turbidity of the cultured system was measured at a wavelength of 600 nm to obtain MIC (μg/ml).

For comparison, MIC of eugenol, a plant component known to have relatively strong antimicrobial activity, against *Propionibacterium acnes* was obtained in the same manner. The results obtained are shown in Table 1 below.

TABLE 1

| Test Compound | MIC (μg/ml) |
| --- | --- |
| Caryophyllene | 3.13 |
| Cedrene | 1.57 |
| Longifolene | 1.57 |
| Thujopsene | 6.25 |
| Eugenol | 50.0 |

As is shown in Table 1, all the active ingredients according to the present invention inhibited growth of *Propionibacterium acnes* at much lower concentrations than eugenol and were thus proved to exhibit powerful antimicrobial activity.

FORMULATION EXAMPLE 1

| | |
| --- | --- |
| 1. Caryophyllene | 0.1 part |
| 2. Glycerin | 2.0 parts |
| 3. 1,3-Butylene glycol | 2.0 parts |
| 4. Sodium citrate | 0.1 part |
| 5. Ethanol | 15.0 parts |
| 6. Polyoxyethylene oleyl alcohol | 0.5 part |
| 7. Paraben | 0.1 part |
| 8. Purified water | remainder |
| Total: | 100.0 parts |

Components 1, 5, 6, and 7 were mixed and dissolved at room temperature. Separately, components 2, 3, 4, and 8 were mixed and dissolved at room temperature. The former mixture was added to the latter mixture, followed by stirring to prepare a cosmetic lotion for treating acne vulgaris.

FORMULATION EXAMPLES 2 TO 4

A cosmetic lotion for treating acne vulgaris was prepared in the same manner as in Formulation Example 1, except for replacing caryophyllene as component 1 with cedrene (Example 2), longifolene (Example 3), or thujopsene (Example 4).

TEST EXAMPLE 2

Antimicrobial Activity of Preparations

Antimicrobial activity against *Propionibacterium acnes* was examined for each of the lotions prepared in Formulation Examples 1 to 4 and comparative lotions prepared in the same manner as in Formulation Example 1 except for replacing caryophylene with eugenol (Comparative Example 1) or using no active ingredient (Comparative Example 2). Each of the lotions under test was added to a sterilized 4.6% aqueous solution of an ABCM bouillon to a final concentration of 2 μl/ml or 5 μl/ml, and a 5 ml aliquot of the system was poured into a test tube. To the test tube was added 0.1 ml of the culture of *Propionibacterium acnes* which had been preliminarily cultured so as to contain about a cell density of $1 \times 10^8$ cells/ml, followed by static-culturing under anaerobic conditions at 37° C. for 48 hours. The turbidity of the cultured system was measured at 600 nm, and the growth of the bacterium was visually observed. The results obtained are shown in Table 2 below. Symbols used in Table 2 have the following meanings.

TABLE 2

| Preparation | Active Ingredient | Growth of Bacterium | |
|---|---|---|---|
| | | 2 μl/ml | 5 μl/ml |
| Example 1 | caryophyllene | + | − |
| Example 2 | cedrene | − | − |
| Example 3 | longifolene | − | − |
| Example 4 | thujopsene | + | − |
| Compara. Example 1 | eugenol | + | + |
| Compara. Example 2 | none | ++ | ++ |

−: The culture was clear with no proliferation of the bacterium being observed.
+: The culture was turbid with proliferation of the bacterium being observed.
++: The culture was considerably turbid with vigorous proliferation of the bacterium being observed.

As can be seen from Table 2, substantially no proliferation of *Propionibacterium acnes* was observed with the lotions for acne vulgaris according to the present invention as compared with the lotion containing eugenol or the control containing no plant component, proving strong antimicrobial activity of the preparations according to the present invention.

| FORMULATION EXAMPLE 5 | |
|---|---|
| 1. Caryophyllene | 0.3 part |
| 2. Dye | 0.003 part |
| 3. 1,3-Butylene glycol | 5.0 parts |
| 4. Bees wax | 2.0 parts |
| 5. Cetanol | 4.0 parts |
| 6. Purified lanolin | 10.0 parts |
| 7. Squalane | 30.0 parts |
| 8. Paraben | 0.1 part |
| 9. Polyoxyethylenesorbitan monolaurate | 2.0 parts |
| 10. Purified water | remainder |
| Total: | 100.0 parts |

Component 3 was added to component 10, the mixture was heated, and the resulting aqueous solution was kept at 70° C. Other components were mixed and heated at 70° C. to dissolve to prepare an oily solution. The aqueous solution was added to the oily solution, and the mixture was preliminarily emulsified and then homogenized in a homo-mixer to obtain an oil-in-water type cream for treating acne vulgaris.

| FORMULATION EXAMPLE 6 | |
|---|---|
| 1. Caryophyllene | 0.2 part |
| 2. Cedrene | 0.3 part |
| 3. Longifolene | 0.2 part |
| 4. Polyethylene glycol 45 | 10.0 parts |
| 5. Liquid paraffin | 12.3 parts |
| 6. Vaseline | 21.0 parts |
| 7. Paraffin wax | 7.0 parts |
| 8. Glycerin | 49.0 parts |
| Total: | 100.0 parts |

The above components were thoroughly mixed to prepare an ointment for acne vulgaris.

| FORMULATION EXAMPLE 7 | |
|---|---|
| 1. Longifolene | 0.1 part |
| 2. Liquid paraffin | 10.0 parts |
| 3. Vaseline | 4.0 parts |
| 4. Stearic acid | 2.0 parts |
| 5. Cetanol | 1.0 part |
| 6. Glycerin monostearate | 2.0 parts |
| 7. Propylene glycol | 7.0 parts |
| 8. Sodium hydroxide | 0.4 part |
| 9. Purified water | remainder |
| Total: | 100.0 parts |

Components 1 to 6 were mixed, heated to dissolve, and maintained at 70° C. to prepare an oily solution. Other components were mixed, dissolved, and maintained at 70° C. to prepare an aqueous solution. The oily solution was added to the aqueous solution, and the mixture was uniformly emulsified in a homo-mixer, followed by cooling to 30° C. while thoroughly stirring to prepare an emulsion for acne vulgaris.

TEST EXAMPLE 3

Efficacy of Treatment of Acne Vulgaris

The preparation obtained in Formulation Example 1 or 7 was applied on the right of the face each of five patients having acne vulgaris on their face twice each in the morning and evening for consecutive 1 month, while a control preparation having the same composition as the preparation of Formulation Example 1 or 7 except for containing no active ingredient was applied on the left of the face in the same manner. At 1 month treatment, the efficacy on acne vulgaris was evaluated by numerically rating the degree of healing on the right face as compared with the left face (control) according to the following rating system and obtaining an average of marks. The results obtained are shown in Table 3 below.

| Rating System for Evaluation: | |
|---|---|
| 4 | Completely healed. |
| 3 | Apparently improved. |
| 2 | Slightly improved. |
| 1 | No difference from control. |

TABLE 4

| Preparation | Marks |
|---|---|
| Formulation Example 1 | 3.2 ± 0.5 |
| Formulation Example 7 | 3.6 ± 0.3 |

The results shown in Table 4 clearly reveal the effectiveness of the acne vulgaris treating topica according to the present invention. No patient suffered from side effects such as skin irritation.

As described and demonstrated above, the topica for treating and preventing acne vulgaris according to the present invention which contains caryophyllene, cedrene, longifolene or thujopsene belonging to sesquiterpene hydrocarbons as an active ingredient exhibits inhibitory or bactericidal activity on *Propionibacterium acnes*, a pathogenic bacterium causing acne vulgaris, and is effective on treatment or prevention of acne vulgaris. The sesquiterpene hydrocarbons used as active ingredients have high antimicrobial activity at relatively low concentrations so that sufficient effects can be produced at a reduced dose level. Moreover, these compounds are obtained from plants and have therefore high safety on use.

While the invention has been described in detail and with reference to specific examples thereof, it will be apparent to one skilled in the art that various changes and modifications can be made therein without departing from the spirit and scope thereof.

What is claimed is:

1. A method of treating or preventing acne vulgaris which comprises topically applying to a patient in an amount effective to inhibit proliferation of *Propionibacterium acnes*, a composition containing, as an active ingredient, at least one compound selected from the group consisting of caryophyllene, cedrene, longifolene and thujopsene, and at least one carrier or diluent acceptable for topical application.

2. The method of treating or preventing acne vulgaris as claimed in claim 1, wherein the composition comprises from 0.001 to 1% by weight of the active ingredient.

3. The method of treating or preventing acne vulgaris as claimed in claim 2, wherein the composition comprises from 0.01 to 1% by weight of the active ingredient.

* * * * *